United States Patent [19]

Lesher

[11] 4,448,780

[45] May 15, 1984

[54] N-(LOWER-ALKYL)-N'-[5-(PYRIDINYL)-2-PYRIDINYL]UREAS AND CARDIOTONIC USE THEREOF

[75] Inventor: George Y. Lesher, Schodack, N.Y.

[73] Assignee: Sterling Drug Inc., New York, N.Y.

[21] Appl. No.: 414,602

[22] Filed: Sep. 3, 1982

[51] Int. Cl.$^3$ .................... C07D 213/22; A61K 31/44
[52] U.S. Cl. ...................................... 424/263; 546/257
[58] Field of Search .......................... 546/257; 424/263

[56] References Cited

U.S. PATENT DOCUMENTS

| 4,276,293 | 6/1981 | Lesher et al. | 424/263 |
| 4,297,360 | 10/1981 | Lesher et al. | 424/263 |
| 4,317,827 | 6/1982 | Lesher et al. | 424/263 |
| 4,331,672 | 5/1982 | Lesher et al. | 546/257 |

FOREIGN PATENT DOCUMENTS 1322318 7/1973 United Kingdom .

OTHER PUBLICATIONS

D. A. Inoyatova et al., [Chem. Absts. 74, 125,360b (1971); Tr. Samarkand. Gos. Univ. 1969, No. 167, 173–174 (Russ.) from Ref. Zh., Khim 1970, Abstr. No. 5Zh482].
Boehmer [C. A. 30, 59504 (1936); Rec. Trav. Chim. 55, 379–391. (1936)].

*Primary Examiner*—Jane T. Fan
*Attorney, Agent, or Firm*—Robert K. Bair; B. Woodrow Wyatt; Paul E. Dupont

[57] ABSTRACT

N-$R_1$-N-(6-R-5-PY-2-pyridinyl)ureas, where $R_1$ is lower-alkyl, R is hydrogen or lower-alkyl, and PY is 4- or 3-pyridinyl or 4- or 3-pyridinyl having one or two lower-alkyl substituents, or acid-addition salts thereof. Said compounds (I) or pharmaceutically acceptable acid-addition salts thereof are useful as cardiotonic agents. The preparation and cardiotonic use of said compounds are shown.

12 Claims, No Drawings

N-(LOWER-ALKYL)-N'-[5-(PYRIDINYL)-2-PYRIDINYL]UREAS AND CARDIOTONIC USE THEREOF

BACKGROUND OF THE INVENTION (a) Field of the Invention

This invention relates to N-alkyl-N'-[5-(pyridinyl)-2-pyridinyl]ureas, their use as cardiotonic agents, and their preparation.

(b) Description of the Prior Art

Lesher, Opalka and Page [U.S. Pat. No. 4,297,360, issued Oct. 27, 1981] show, inter alia, as cardiotonic agents and as intermediates, 5-(pyridinyl)pyridin-2-amines, e.g., 5-(4-pyridinyl)pyridin-2-amine, alternatively named [3,4'-bipyridin]-6-amine, which are used herein as intermediates.

Lesher, Opalka and Page [U.S. Pat. No. 4,276,293, issued June 30, 1981] show, inter alia, as intermediates, 5-(pyridinyl)pyridin-2-amines, e.g., 5-(4-pyridinyl)pyridin-2-amine.

D. A. Inoyatova et al. [Chem. Absts. 74, 125,360b (1971); Tr. Samarkand. Gos. Univ. 1969, No. 167, 173–4 (Russ.) From Ref. Zh., Khim 1970, Abstr. No. 5Zh482] report the amination of 3,3'-bipyridine and subsequent thin-layer chromatography using diethyl ether to produce 6-amino-3,3'-bipyridine, alternatively named 5-(3-pyridinyl)pyridin-2-amine.

Lesher and Gruett [British Pat. No. 1,322,318, published July 4, 1973] show as intermediates for preparing antibacterially active 1-alkyl-1,4-dihydro-4-oxo-7-PY-1,8-naphthyridine-3-carboxylic acids and esters (where PY is 4- or 3-pyridinyl or 4- or 3-pyridinyl having one or two lower-alkyl substitutents) 2-amino-6-(4- or 3-pyridinyl)pyridine, alternatively named 6-(4- or 3-pyridinyl)pyridin-2-amines.

Lesher and Page [U.S. Pat. No. 4,317,827, issued Mar. 2, 1982] show inter alia, N-[4-(4-pyridinyl)phenyl]-urea, useful as a cardiotonic, and its preparation by reacting 4-(4-pyridinyl)benzeneamine with potassium cyanate in warm aqueous acetic acid solution.

Boehmer [C.A. 30, 5950$^4$ (1936); Rec. trav. chim. 55, 379–91 (1936)] shows the reaction of pyridin-2-amine with lower-alkyl isocyanates to produce N-alkyl-N'-(2-pyridinyl)ureas where alkyl is methyl, n-propyl, isopropyl, n-butyl and isobutyl.

SUMMARY OF THE INVENTION

In a composition of matter aspect, the invention resides in N-$R_1$-N'-(6-R-5-PY-2-pyridinyl)urea or acid-addition salt thereof, useful as a cardiotonic agent, where R, $R_1$ and PY are defined hereinbelow.

In a process aspect the invention resides in the process which comprises reacting 6-R-5-PY-pyridin-2-amine with a lower-alkyl isocyanate to produce said N-$R_1$-N'-(6-R-5-PY-2-pyridinyl)urea.

A composition aspect of the invention resides in a cardiotonic composition for increasing cardiac contractility, said composition comprising a pharmaceutically acceptable carrier and, as the active ingredient thereof, a cardiotonically effective amount of N-$R_1$-N'-(6-R-5-PY-2-pyridinyl)urea or pharmaceutically acceptable acid-addition salt thereof.

In a method aspect the invention resides in the method for increasing cardiac contractility in a patient requiring such treatment which comprises administering to said patient a medicament comprising a pharmaceutically acceptable carrier and, as the active component thereof, a cardiotonically effective amount of N-$R_1$-N'-(6-R-5-PY-2-pyridinyl)urea or pharmaceutically acceptable acid-addition salt thereof.

DETAILED DESCRIPTION INCLUSIVE OF PREFERRED EMBODIMENTS

In a composition of matter aspect the invention resides in N-$R_1$-N'-(6-R-5-PY-2-pyridinyl)urea having the formula I

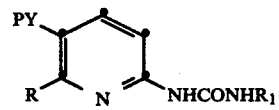

or acid-addition salt thereof, where $R_1$ is lower-alkyl, R is hydrogen or lower-alkyl and PY is 4-pyridinyl or 3-pyridinyl, or 4-pyridinyl or 3-pyridinyl having one or two lower-alkyl substituents. Preferred embodiments are the compounds of formula I where PY is 4-pyridinyl, R is methyl or ethyl, and $R_1$ is alkyl having from one to four carbon atoms. Particularly preferred embodiments are the compounds of formula I where PY is 4-pyridinyl, R is methyl and $R_1$ is methyl or ethyl. The compounds of formula I are useful as cardiotonic agents, as determined by standard pharmacological evaluation procedures.

A process aspect of the invention resides in the process which comprises reacting 6-R-5-PY-pyridin-2-amine with a lower-alkyl isocyanate having the formula $R_1$NCO to produce the compound having formula I. Preferred and particularly preferred process embodiments reside in the preparation of the corresponding preferred and particularly preferred compounds of formula I. The process is preferably run in the presence of a strong base, preferably sodium hydride.

A composition aspect of the invention resides in the cardiotonic composition for increasing cardiac contractility, said composition comprising a pharmaceutically acceptable carrier and, as the active component thereof, a cardiotonically effective amount of the compound having formula I or a pharmaceutically acceptable acid-addition salt thereof. Preferred and particularly preferred composition embodiments reside in the compositions having as active components, the preferred and particularly preferred compounds of formula I.

A method aspect of the invention resides in the method for increasing cardiac contractility in a patient requiring such treatment which comprises administering orally or parenterally in solid or liquid dosage form to such patient a cardiotonically effective amount of the compound of formula I or pharmaceutically acceptable acid-addition salt thereof. Preferred and particularly preferred method embodiments reside in the methods using as active components, the preferred and particularly preferred compounds of formula I.

The term "lower-alkyl" as used herein, e.g., as one of the meanings for R or $R_1$ or as a substituent for PY in formula I, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-pentyl, n-hexyl, and the like.

Illustrative of PY in formula I where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl and the like.

The compounds having formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds having formula I were assigned on the basis of evidence provided by infrared, nuclear magnetic resonance and mass spectra, and by the correspondence of calculated and found values for the elementary analyses.

The manner of making and using the instant invention will now be generally described so as to enable a person skilled in the art of pharmaceutical chemistry to make and use the same, as follows.

The reaction of 6-R-5-PY-pyridin-2-amine with a lower alkyl isocyanate to produce N-$R_1$-N'-(6-R-5-PY-2-pyridinyl)urea is carried out preferably by stirring the reactants in the presence of a strong base, preferably sodium hydride and preferably in an aprotic solvent with cooling and then stirring the reaction mixture at room temperature. The aprotic solvent preferably used is dimethylformamide; other suitable solvents include tetrahydrofuran and benzene. In place of sodium hydride there can be used sodamide or lithium diisopropylamide. The reaction can be carried out by slowly adding the strong base, e.g., sodium hydride, to a cooled mixture of the reactants or, alternatively, by first slowly adding said base to the 6-R-5-PY-pyridin-2-amine with cooling and then adding the lower-alkyl isocyanate.

The intermediate 6-R-5-PY-pyridin-2-amines are prepared by generally known procedures described in said U.S. Pat. Nos. 4,276,293 and 4,297,360 and said Inoyatova et al reference, Chem. Abstrs. 74, 125,360b (1971), and are further illustrated hereinbelow in the specific exemplary disclosure.

The following examples will further illustrate the invention without, however, limiting it thereto.

A. INTERMEDIATE 6-R-5-PY-PYRIDIN-2-AMINES

A-1. 5-(4-Pyridinyl)pyridin-2-amine, alternatively named [3,4'-bipyridin]-6-amine - A mixture containing 48 g of 2-chloro-5-(4-pyridinyl)pyridine and 700 ml of ammonium hydroxide was heated in an autoclave at 150° C. and 200 p.s.i. for sixteen hours. The solid was collected, washed with water and dried. The filtrate was distilled in vacuo to remove the excess ammonium hydroxide and the remaining residue was combined with the above solid and the combined material was recrystallized from water and dried in vacuo at 70° C. to yield 29 g of 5-(4-pyridinyl)pyridin-2-amine, m.p. 192°–195° C.

A-2. 6-Methyl-5-(4-pyridinyl)pyridin-2-amine—A mixture containing 17.4 g of 2-chloro-6-methyl-5-(4-pyridinyl)pyridine and 60 ml of 95% hydrazine was heated on a steam bath for 24 hours and chilled. The separated solid was collected by filtration and washed successively with water and acetonitrile to yield 15.8 g of 6-methyl-5-(4-pyridinyl)pyridine-2-hydrazine, which was used directly without further purification to prepare the corresponding substituted-pyridin-2-amine as described in the following paragraph. A sample of 6-methyl-5-(4-pyridinyl)pyridine-2-hydrazine recrystallized from absolute ethanol and dried in a vacuum oven at 80° C. melted at 164°–165° C.

A mixture containing 8.5 g of 6-methyl-5-(4-pyridinyl)pyridine-2-hydrazine, 3 g of Raney nickel and 200 ml of methanol was placed in a Parr hydrogenation apparatus and treated at 60° C. under catalytic hydrogenation conditions for eight hours and then allowed to cool. The reaction mixture was filtered and the filtrate concentrated in vacuo to remove the solvent. The solid residue was slurried with acetonitrile, collected, recrystallized from propionitrile using decolorizing charcoal and dried to produce 4.7 g of 6-methyl-5-(4-pyridinyl)-pyridin-2-amine, m.p. 207°–209° C.

Following the procedure described in Example A-1 but using in place of 2-chloro-5-(4-pyridinyl)pyridine a molar equivalent quantity of the appropriate 2-chloro-5-PY-pyridine, it is contemplated that the corresponding 5-PY-pyridin-2-amines of Examples A-3 through A-6 can be obtained.

A-3. 5-(2-Methyl-4-pyridinyl)pyridin-2-amine.
A-4. 5-(3-Ethyl-4-pyridinyl)pyridin-2-amine.
A-5. 5-(3-Pyridinyl)pyridin-2-amine.
A-6. 5-(6-Methyl-3-pyridinyl)pyridin-2-amine.

Following the procedure described in Example A-2 but using in place of 2-chloro-6-methyl-5-(4-pyridinyl)-pyridine a molar equivalent quantity of the appropriate 2-chloro-6-Q-5-PY-pyridine, it is contemplated that the corresponding 6-Q-5-PY-pyridin-2-amines of Examples A-7 through A-16 can be obtained.

A-7. 6-Ethyl-5-(4-pyridinyl)pyridin-2-amine.
A-8. 6-Methyl-5-(3-pyridinyl)pyridin-2-amine.
A-9. 6-n-Propyl-5-(4-pyridinyl)pyridin-2-amine.
A-10. 6-Isopropyl-5-(4-pyridinyl)pyridin-2-amine.
A-11. 6-n-Butyl-5-(4-pyridinyl)pyridinyl-2-amine.
A-12. 6-Isobutyl-5-(4-pyridinyl)pyridin-2-amine.
A-13. 5-(4-Pyridinyl)-6-tert.-butylpyridin-2-amine.
A-14. 6-n-Pentyl-5-(4-pyridinyl)pyridin-2-amine.
A-15. 6-Ethyl-5-(2-methyl-4-pyridinyl)pyridin-2-amine.
A-16. 6-Ethyl-5-(2-methyl-3-pyridinyl)-pyridin-2-amine.

B. N-(R)-N'-(6-R-5-PY-2-PYRIDINYL)UREAS

B-1. N-Methyl-N'-[6-methyl-5-(4-pyridinyl)-2-pyridinyl]urea—To a mixture containing 5 g of 50% sodium hydride (in mineral oil) suspended in 50 ml of dimethylformamide was added 11.5 g of 6-methyl-5-(4-pyridinyl)pyridin-2-amine and the mixture was stirred for an additional ten minutes. To the stirred mixture was added 6 ml of methyl isocyanate with stirring at room temperature. After about fifteen minutes, a vigorous exothermic reaction ensued. The reaction mixture was evaporated to dryness in vacuo, methanol was added and evaporated off in vacuo and to the residue was added methanol which again was evaporated off in vacuo. To the residue was added water and the solid was collected, washed successively with n-hexane and acetonitrile, recrystallized from dioxane and dried to yield 2.5 g of N-methyl-N'-[6-methyl-5-(4-pyridinyl)-2-pyridinyl]urea, alternatively named N-methyl-N'-[2-methyl-(3,4'-bipyridin)-6-yl]urea, m.p. 213°–214° C.

Acid-addition salts of N-methyl-N'-[6-methyl-5-(4-pyridinyl)-2-pyridinyl]urea are conveniently prepared by adding to a mixture of 1 g of N-methyl-N'-[6-methyl-5-(4-pyridinyl)-2-pyridinyl]urea in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partially evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of N-methyl-N'-[6-methyl-5-(4-pyridinyl)-2-pyridinyl]urea and the appropriate acid, e.g., lactic acid or hydrochloric acid, to prepare respectively the lactate or hydrochloride salt of N-methyl-N'-[6-methyl-5-(4-pyridinyl)-2-pyridinyl]urea in aqueous solution.

B-2. N-n-Butyl-N'-[6-methyl-5-(4-pyridinyl)-2-pyridinyl]urea—To a stirred mixture containing 2.88 g of 50% sodium hydride (in mineral oil) suspended in 50 ml of dimethylformamide was added 10.3 g of 6-methyl-5-(4-pyridinyl)pyridin-2-amine and the resulting mixture was stirred for 30 minutes at room temperature and cooled in an ice bath. To the cold mixture was added with stirring 9.0 g of n-butyl isocyanate and the resulting mixture was stirred for 2 hours in an ice bath and then for another four hours at room temperature. The reaction mixture was concentrated to dryness in vacuo and the residue was taken up with cold 6N hydrochloric acid. The acidic solution was extracted with n-hexane and then made basic with concentrated ammonium hydroxide solution. The resulting oil that separated crystallized and was extracted with three portions of methylene dichloride. The methylene dichloride solvent was distilled off in vacuo and the remaining solid residue was recrystallized twice from acetonitrile, using decolorizing charcoal the second time, to produce 8.8 g of N-n-butyl-N'-[6-methyl-5-(4-pyridinyl)-2-pyridinyl]urea, m.p. 164°–165° C.

B-3. N-(tert.-butyl)-N'-[6-methyl-5-(4-pyridinyl)-2-pyridinyl]urea—To a stirred mixture containing 17 g of 6-methyl-5-(4-pyridinyl)pyridin-2-amine, 80 ml of dimethylformamide and 20 ml of tert.-butyl isocyanate in an ice bath was slowly added over a 20 minute period 5 g of sodium hydride and the reaction mixture was stirred for 1 hour. The ice bath was then removed and the reaction mixture was stirred at room temperature for another 4 hours and allowed to stand at room temperature overnight. The reaction mixture was poured cautiously into a mixture containing 400 ml of ice water and 11 ml of acetic acid. The solid that separated was collected, washed successively with water and cyclohexane and then dried in a vacuum oven at 60° C. The product was then recrystallized from acetonitrile and dried in a vacuum oven at 60° C. overnight to produce 14 g of N-(tert.-butyl)-N'-[6-methyl-5-(4-pyridinyl)-2-pyridinyl]urea, m.p. 297°–300° C. with decomposition.

Following the procedure described in Example B-3 but using in place of 6-methyl-5-(4-pyridinyl)pyridin-2-amine and tert-butyl isocyanate molar equivalent quantities of the appropriate 6-R-5-PY-pyridin-2-amine and lower-alkyl isocyanate respectively, it is contemplated that the corresponding N-$R_1$-N'-(6-R-5-PY-pyridinyl)ureas of Examples B-4 through B-17 can be obtained.

B-4. N-Ethyl-N'-[5-(2-methyl-4-pyridinyl)-2-pyridinyl]urea.
B-5. N'-[5-(3-Ethyl-4-pyridinyl)-2-pyridinyl]-N-n-propylurea.
B-6. N-n-Pentyl-N'-[5-(3-pyridinyl)-2-pyridinyl]urea.
B-7. N-(n-Hexyl)-N'-[5-(6-methyl-3-pyridinyl)-2-pyridinyl]urea.
B-8. N'-[6-Ethyl-5-(4-pyridinyl)-2-pyridinyl]-N-methylurea.
B-9. N-Ethyl-N'-[6-methyl-5-(3-pyridinyl)-2-pyridinyl]urea.
B-10. N-Methyl-N'-[6-n-propyl-5-(4-pyridinyl)-2-pyridinyl]urea.
B-11. N-Isopropyl-N'-[6-isopropyl-5-(4-pyridinyl)-2-pyridinyl]urea.
B-12. N'-[6-n-Butyl-5-(4-pyridinyl)-2-pyridinyl]-N-methylurea.
B-13. N'-[6-Isobutyl-5-(4-pyridinyl)-2-pyridinyl]-N-methylurea.
B-14. N-Ethyl-N'-[5-(4-pyridinyl)-6-tert.-butyl-2-pyridinyl]urea.
B-15. N-Methyl-N'-[6-n-pentyl-5-(4-pyridinyl)-2-pyridinyl]urea.
B-16. N'-[6-Ethyl-5-(2-methyl-4-pyridinyl)-2-pyridinyl]-N-methylurea.
B-17. N'-[6-Ethyl-5-(2-methyl-3-pyridinyl)-2-pyridinyl]-N-methylurea.

The usefulness of the compounds of formula I, or pharmaceutically acceptable acid-addition salts thereof, as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formula I or pharmaceutically acceptable acid-addition salts thereof at doses of 1, 3, 10, 30 and/or 100 μg./ml., were found to cause significant increases, that is, greater than 25% (cat) or 30% (guinea pig) in papillary muscle force and significant increases, that is, greater than 25% (cat) or 30% (guinea pig), in right atrial force, while causing a lower percentage increase in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested by this procedure in the cat, the compound of Example B-3, namely N-(tert.-butyl)-N'-[5-(4-pyridinyl)-2-pyridinyl]urea, was found to cause respective increases in papillary muscle force of 70%, 53% and 138% at doses of 10, 30 and 100 μg/ml. When tested by this procedure in the guinea pig, the compound of Example B-1, namely, N-methyl-N'-[6-methyl-5-(4-pyridinyl)pyridinyl]urea, was found to cause respective increases in papillary muscle force of 57%, 129% and 196% at doses of 1, 3 and 10 μg/ml; and, the compound of Example B-2, namely, N-(n-butyl)-N'-[6-methyl-5-(4-pyridinyl)-2-pyridinyl]urea was found to cause respective increases in papillary muscle force of 86% and 79% at 10 and 30 μg/ml.

When tested by said anesthetized dog procedure, the compounds of the invention or said salts thereof at doses of 0.1, 0.3, and 1.0 mg./kg. administered intravenously were found to cause significant increases, that is, 25% or greater, in cardiac contractile force or cardiac contractility with lower changes in heart rate and blood pressure. For example, the compound of Example B-1 was found to cause respective increases of 49%, 113% and 154% in contractile force at doses of 0.1, 0.3 and 1.0 mg/kg.

The present invention includes within its scope a cardiotonic composition for increasing cardiac contractility, said composition comprising a pharmaceutically acceptable carrier and, as the active component thereof, a cardiotonically effective amount of the compound of formula I or said salt thereof. The invention also includes within its scope the method for increasing cardiac contractility in a patient requiring such treatment which comprises administering to such patient said cardiotonic composition providing a cardiotonically effective amount of the compound of formula I or said salt thereof. In clinical practice said compound will normally be administered orally or parenterally in a wide variety of dosage forms.

Solid compositions for oral admininstration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such a magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. N-R$_1$-N'-(6-R-5-PY-2-pyridinyl)urea having the formula

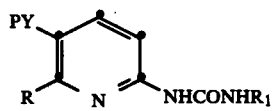

or an acid-adddition salt thereof, where R$_1$ is lower-alkyl, R is hydrogen or lower-alkyl, and PY is 4-pyridinyl or 3-pyridinyl, or 4-pyridinyl or 3-pyridinyl having one or two lower-alkyl substituents.

2. A compound according to claim 1 where PY is 4-pyridinyl, R is methyl or ethyl and R$_1$ is alkyl having one to four carbon atoms.

3. A compound according to claim 1 where PY is 4-pyridinyl, R is methyl and R$_1$ is methyl or ethyl.

4. N-Methyl-N'-[6-methyl-5-(4-pyridinyl)-2-pyridinyl]urea according to claim 1 or an acid-addition salt thereof.

5. A cardiotonic composition for increasing cardiac contactility, said composition comprising a pharmaceutically acceptable carrier and, as the active component thereof, a cardiotonically effective amount of the compound of claim 1 or a pharmaceutically acceptable acid-addition salt thereof.

6. A composition according to claim 5 where the active component is N-R$_1$-N'-[6-R-5-(4-pyridinyl)-2-pyridinyl]urea where R is methyl or ethyl and R$_1$ is alkyl having from one to four carbon atoms, or a pharmaceutically acceptable acid-addition salt thereof.

7. A composition according to claim 5 where the active component is N-R$_1$-N'-[6-methyl-5-(4-pyridinyl)-2-pyridinyl]urea where R$_1$ is methyl or ethyl, or a pharmaceutically acceptable acid-addition salt thereof.

8. A composition according to claim 5 where the active component is N-methyl-N'-[6-methyl-5-(4-pyridinyl)-2-pyridinyl]urea or pharmaceutically acceptable acid-addition salt thereof.

9. The method for increasing cardiac contractility in a patient requiring such treatment which comprises administering orally or parenterally in a solid or liquid dosage form to such patient a cardiotonically effective amount of the compound of claim 1 or pharmaceutically acceptable acid-addition salt thereof.

10. The method according to claim 9 where the active component is N-R$_1$-N'-[6-R-5-(4-pyridinyl)-2-pyridinyl]urea where R is methyl or ethyl and R$_1$ is alkyl having from one to four carbon atoms, or a pharmaceutically acceptable acid-addition salt thereof.

11. The method according to claim 9 where the active component is N-R$_1$-N-[6-methyl-5-(4-pyridinyl)-2-pyridinyl]urea where R$_1$ is methyl or ethyl, or a pharmaceutically acceptable acid-addition salt thereof.

12. The method according to claim 9 where the active component is N-methyl-N'-[6-methyl-5-(4-pyridinyl)-2-pyridinyl]urea or pharmaceutically acceptable acid-addition salt thereof.

* * * * *